(12) United States Patent
Kumar et al.

(10) Patent No.: US 6,337,396 B1
(45) Date of Patent: Jan. 8, 2002

(54) PROCESS FOR PREPARING CRYSTALLINE CEFADROXIL HEMIHYDRATE FROM CEFADROXIL DIMETHYLFORMAMIDE SOLVATE

(75) Inventors: Yatendra Kumar; Shailendra Kumar Singh, both of Haryana (IN)

(73) Assignee: Ranbaxy Laboratories Limited, New Delhi (IN)

( * ) Notice: Subject to any disclaimer, the term of this patent is extended or adjusted under 35 U.S.C. 154(b) by 0 days.

(21) Appl. No.: 09/460,452

(22) Filed: Dec. 13, 1999

(30) Foreign Application Priority Data

Jul. 14, 1999 (IN) .................................................. 969/99

(51) Int. Cl.$^7$ ............................................ C07D 501/22
(52) U.S. Cl. ...................................................... 540/230
(58) Field of Search ......................................... 540/230

(56) References Cited

U.S. PATENT DOCUMENTS

| | | | |
|---|---|---|---|
| 3,489,752 A | 1/1970 | Crast | 540/230 |
| 3,985,741 A | 10/1976 | Crast, Jr. et al. | 540/230 |
| 4,504,657 A | 3/1985 | Bouzard et al. | 540/230 |
| 4,962,195 A | 10/1990 | Marsili et al. | 540/230 |
| 5,023,331 A | 6/1991 | Marsili et al. | 540/230 |

FOREIGN PATENT DOCUMENTS

| | | | |
|---|---|---|---|
| EP | 0 287 751 B1 | | 12/1994 |
| WO | 91/00865 | * | 1/1991 |

* cited by examiner

Primary Examiner—Mark L Berch
(74) Attorney, Agent, or Firm—Jaydeep R. Deshmukh

(57) ABSTRACT

A method for preparing crystalline cefadroxil hemihydrate from cefadroxil dimethyl formamide solvate using a mixture of a lower alkanol and water.

4 Claims, No Drawings

PROCESS FOR PREPARING CRYSTALLINE CEFADROXIL HEMIHYDRATE FROM CEFADROXIL DIMETHYLFORMAMIDE SOLVATE

FIELD OF THE INVENTION

The present invention relates to a method for preparing crystalline cefadroxil hemihydrate.

BACKGROUND OF THE INVENTION

Cefadroxil is chemically 7-[D-α-amino-α-(p-hydroxyphenyl)acetamido]-3-methyl-3-cephem-4-carboxylic acid. It is a well-known antibiotic substance having antibacterial activity and is disclosed in U.S. Pat. No. 3,489,752. U.S. Pat. No. 3,985,741 discloses preparation of cefadroxil by acylation of 7-aminodesacetoxycephalosporanic acid with the mixed anhydride of D-(−)-α-(p-hydroxyphenyl)glycine when the latter's α-amino group has been blocked with a β-keto compound such as methyl acetoacetate.

U.S. Pat. No. 4,504,657 claims a different form of cefadroxil that is the crystalline form of cefadroxil, known as cefadroxil monohydrate having a well-defined X-ray diffraction pattern. This crystalline cefadroxil monohydrate is obtained by acylation of silylated 7-aminodesacetoxycephalosporanic acid with D(−)α-amino-α-(p-hydroxyphenyl)acetyl chloride hydrochloride.

U.S. Pat. No. 4,962,195 discloses yet another novel crystalline cefadroxil having a water content of about 3% and characterized by distinct X-ray diffraction properties. This novel cefadroxil is called "cefadroxil hemihydrate" and is shown to be more stable than crystalline cefadroxil monohydrate.

U.S. Pat. Nos. 4,962,195 and 5,023,331 disclose a method of producing cefadroxil hemihydrate by adding to an aqueous solution containing cefadroxil prepared from 7-aminodesacetoxycephalosporanic acid, a solvent selected from the group consisting of dimethylacetamide, monomethylformamide or N-methyl-2-pyrrolidone at a controlled pH (5.5 to 6.0) to give the corresponding cefadroxil solvate which precipitates and is filtered off. After the cefadroxil solvate is dried, it is slurried with a mixture of methanol-isopropyl alcohol 30:70 to 50:50 by volume at a temperature in the range of 45° C. to 55° C., to give crystalline cefadroxil hemihydrate which is isolated by filtration.

Both of these patents report that the use of the cefadroxil solvates of dimethylacetamide, of N-methyl-2-pyrrolidone and of monomethylformamide is critical for the preparation of crystalline cefadroxil hemihydrate and that it was impossible to obtain the desired crystalline cefadroxil hemihydrate from the known cefadroxil dimethyl formamide solvate (U.S. Pat. Nos. 3,985,741, 4,504,657 and U.S. Pat. No. Re. 31,730). It always resulted in the isolation of the known crystalline cefadroxil monohydrate due to the fact that the cefadroxil dimethyl formamide solvate has a K.F. value of 1.8% or more.

The use of cefadroxil solvates as disclosed in U.S. Pat. Nos. 4,962,195 and 5,023,331 pose serious problems of filterability at a commercial manufacturing scale and the solvents used are quite expensive. These disadvantages make the process operationally tedious and inefficient cost-wise.

It is an object of the present invention to solve the problems associated with the prior art. According to one aspect, the present invention provides an efficient method for the preparation of cefadroxil hemihydrate from cefadroxil dimethyl formamide solvate. The process provides obvious benefits with respect to economics and convenience to operate at a large scale.

The present invention specifically describes a method for producing crystalline cefadroxil hemihydrate of Formula II, from cefadroxil dimethyl formamide solvate which comprises slurrying cefadroxil dimethyl formamide solvate of Formula I, with a mixture of a lower alkanol and water, at a temperature in the range of about 40° C. to 50° C., and isolating the crystalline cefadroxil hemihydrate from the reaction mixture.

Lower alkanol is selected from methanol, n-propanol, isopropanol and mixtures thereof. Cefadroxil dimethyl formamide solvate is dried to preferably achieve a water content less than 1.8%. Crystalline cefadroxil hemihydrate can be isolated by any means such as filtration, decantation, centrifugation or filtration under vacuum. Crystalline cefadroxil hemihydrate is preferably isolated by filtration.

U.S. Pat. No. 4,962,195 and 5,023,331 report that the use of the mixture methanol/isopropyl alcohol has proved to be essential to give the desired cefadroxil hemihydrate and if ethyl alcohol is used, the cefadroxil molecule is decomposed. The use of methanol alone gives an exceedingly high amount of residual methanol (more than 0.4%).

SUMMARY OF THE INVENTION

It has been surprisingly found when mixture of methanol and water is used, cefadroxil hemihydrate with a methanol content less than 0.2% is obtained, as opposed to the use of methanol above. Use of a single solvent over a mixture of solvents gives the obvious benefits with respect to the recovery of solvent and thus is more economical.

According to another aspect of the invention, a single solvent is used in the preparation of cefadroxil hemihydrate from cefadroxil dimethyl formamide solvate.

Cefadroxil dimethyl formamide solvate of Formula I:

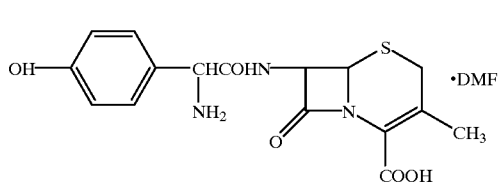

is prepared by the methods known in the art, specifically example 2A of U.S. Pat. No. 4,504,657.

The present invention is illustrated by the following example, which is not intended to limit the effective scope of the claims.

DETAILED DESCRIPTION OF THE INVENTION

EXAMPLE

Crystalline Cefadroxil Hemihydrate

Cefadroxil dimethyl formamide solvate (101 g) was slurried in methanol (570 ml) and water (30 ml) at 40–45° C. for 30 minutes. It was further stirred for 2 hours and then cooled to 20–25° C. The precipitated product was filtered and washed with acetone (200 ml) to give crystalline cefadroxil hemihydrate.

Yield: 60.4 g,
Moisture (By K.F.): 3.6%,
HPLC Assay: 97% as is basis
Residual methanol: 0.1%

While the present invention has been described in terms of its specific embodiments, certain modifications and equivalents will be apparent to those skilled in the art and are intended to be included within the scope of the present invention.

We claim:

1. A method for preparing crystalline cefadroxil hemihydrate of Formula II:

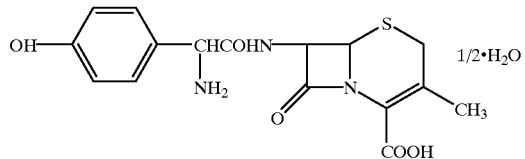

II which comprises slurrying cefadroxil dimethyl formamide solvate of Formula I:

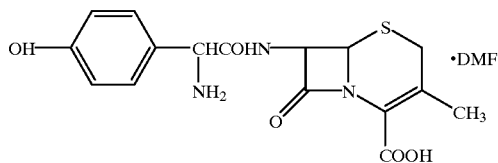

I having a water content less than 1.8% with a mixture (95:5 by volume) of a lower alkanol and water, at a temperature in the range of about 40° C. to 45° C., for about two hours and isolating the crystalline cefadroxil hemihydrate from the reaction mixture.

2. The process of claim 1 wherein the lower alkanol is selected from the group consisting of methanol, n-propanol, isopropanol and mixtures thereof.

3. The process of claim 1 wherein the lower alkanol is methanol.

4. The process of claim 1 wherein said crystalline cefadroxil hemihydrate is isolated by filtration.

* * * * *